United States Patent
Palmer

(10) Patent No.: US 10,463,830 B2
(45) Date of Patent: Nov. 5, 2019

(54) PACKAGED URINARY CATHETER WITH DISPENSING CONTROL DEVICE

(71) Applicant: CURE MEDICAL, LLC, Newport Beach, CA (US)

(72) Inventor: Timothy Palmer, Stillwater, MN (US)

(73) Assignee: CURE MEDICAL, LLC, Newport Beach, CA (US)

(*) Notice: Subject to any disclaimer, the term of this patent is extended or adjusted under 35 U.S.C. 154(b) by 182 days.

(21) Appl. No.: 15/642,431

(22) Filed: Jul. 6, 2017

(65) Prior Publication Data
US 2019/0009051 A1    Jan. 10, 2019

(51) Int. Cl.
*A61M 25/00* (2006.01)
*A61M 25/01* (2006.01)
*A61M 27/00* (2006.01)

(52) U.S. Cl.
CPC ...... *A61M 25/002* (2013.01); *A61M 25/0113* (2013.01); *A61M 27/00* (2013.01)

(58) Field of Classification Search
CPC .... A61M 25/00; A61M 25/002; A61M 25/01; A61M 25/017; A61M 25/0113; A61M 27/00; A61M 2202/0496; A61M 2209/06
USPC .......... 206/363, 364; 604/327, 328, 540–544
See application file for complete search history.

(56) References Cited

U.S. PATENT DOCUMENTS

| | | |
|---|---|---|
| 836,303 A | 11/1906 | Christensen |
| 1,206,655 A | 11/1916 | Belcher |
| 2,131,956 A | 10/1938 | Jones |
| 2,221,801 A | 11/1940 | Keppinger |
| 2,422,891 A | 6/1947 | Dickson |
| 2,584,644 A | 2/1952 | Verdi |
| 2,894,119 A | 7/1959 | Stenger |
| 3,365,761 A | 1/1968 | Kalvig |
| 4,141,452 A | 2/1979 | Martin et al. |
| 4,230,115 A | 10/1980 | Walz, Jr. et al. |
| 5,108,066 A | 4/1992 | Lundstrom |
| 5,224,681 A | 7/1993 | Lundstrom |
| D358,679 S | 5/1995 | Garrity |
| 5,454,798 A | 10/1995 | Kubalak et al. |
| 5,529,148 A | 6/1996 | O'Leary |
| 5,603,702 A | 2/1997 | Smith et al. |
| 5,690,645 A | 11/1997 | Van Erp |
| 5,993,437 A | 11/1999 | Roaz |
| 6,004,305 A | 12/1999 | Hursman et al. |
| 6,010,105 A | 1/2000 | Davis |
| 6,053,905 A | 4/2000 | Daignault, Jr. et al. |
| 6,179,514 B1 | 1/2001 | Cheng |
| 6,402,726 B1 | 6/2002 | Genese |

(Continued)

*Primary Examiner* — Bryon P Gehman
(74) *Attorney, Agent, or Firm* — Sherrill Law Offices, PLLC

(57) ABSTRACT

A catheter movement control device and packaged catheter equipped with the catheter movement control device. The catheter movement control device includes a main body defining a passageway and a locking member with an oblong orifice hingedly attached to the main body. The locking member pivots about a pivot axis and is rotationally secured to the main body so that the major axis of the oblong orifice is fixedly oriented nearly parallel with the pivot axis. The locking member is pivotable about the pivot axis relative to the main body as between a first position wherein the orifice is aligned with the passageway, and a second position wherein the orifice is misaligned with the passageway.

19 Claims, 6 Drawing Sheets

(56) References Cited

U.S. PATENT DOCUMENTS

| | | | |
|---|---|---|---|
| 6,427,964 B1 | 8/2002 | Hillstrom et al. | |
| 6,578,709 B1 | 6/2003 | Kavanagh et al. | |
| 6,602,244 B2 | 8/2003 | Kavanagh et al. | |
| 7,458,964 B2 | 12/2008 | Mosler et al. | |
| 8,734,426 B2 * | 5/2014 | Ahmed | A61M 25/04 604/544 |
| 9,011,413 B2 | 4/2015 | Chung | |
| 9,782,563 B2 * | 10/2017 | Palmer | A61M 25/0111 |
| 10,052,454 B2 * | 8/2018 | Palmer | A61M 25/0017 |
| 2003/0050653 A1 | 3/2003 | Berger | |
| 2007/0073222 A1 | 3/2007 | Lilley, Jr. et al. | |
| 2007/0225649 A1 | 9/2007 | House | |
| 2008/0103464 A1 | 5/2008 | Mosler et al. | |
| 2010/0312227 A1 | 12/2010 | House | |
| 2011/0098682 A1 | 4/2011 | Ahmed et al. | |
| 2013/0110087 A1 | 5/2013 | Kane | |
| 2014/0257250 A1 | 9/2014 | Palmer | |
| 2014/0276661 A1 | 9/2014 | Hannon et al. | |
| 2015/0352321 A1 | 12/2015 | Hannon et al. | |
| 2015/0352324 A1 | 12/2015 | Palmer | |

\* cited by examiner

PACKAGED URINARY CATHETER WITH DISPENSING CONTROL DEVICE

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need single use catheters have been developed to allow patients to perform self catheterization. To aid in the insertion of the catheter in a body cavity they are often lubricated making the handling of the catheter difficult and messy. Many catheter packages are now designed to aid in the use of the catheter and at least the funnel end of the catheter is retained in the package. This allows the user to use the package to manipulate the catheter and avoid the messy and possible insanitary handling of the actual catheter. Manipulating a slippery catheter through a plastic bag can be quite difficult even for someone with excellent dexterity. To aid in the manipulation of the catheter various devices have been conceived to limit or control the movement of the catheter into and out of its package.

One such device is disclosed in U.S. Pat. No. 7,458,964 to Mosler et al. Mosler et al. discloses a catheter movement control device in which the catheter passes through a locking ring retained within the passage of a housing wherein the locking ring can be tilted within the passageway as between an aligned position for allowing passage of the catheter through the passage when the catheter is translated through the passage in a first direction, and a misaligned position for resisting passage of the catheter through the passage when the catheter is translated through the passage in a second opposite direction. Mosler et al. discloses various embodiments of the locking ring with differently shaped orifices through the locking ring, including an oval orifice.

The oval orifice embodiment of Mosler et al. suffers frequent failure as the locking ring, which is free to rotate within the passage, tends to quickly rotate into the rotational position which provides a path of least resistance (i.e., the major axis of the oval orifice perpendicular to the pivot axis of the ring), resulting in a loss of resistance to movement of the catheter in the second direction.

SUMMARY OF THE INVENTION

A first aspect of the invention is a catheter movement control device that includes a main body and a locking member. A passageway extends through the main body and an oblong orifice extends through the locking member. The locking member is hingedly attached to the main body for pivoting about a pivot axis and is fixedly secured to the main body so that the major axis of the oblong orifice is fixedly oriented nearly parallel with the pivot axis. The locking member is pivotable about the pivot axis relative to the main body as between a first position wherein the central axis of the orifice is aligned with the central axis of the passageway, and a second position wherein the central axis of the orifice is misaligned with the central axis of the passageway.

A second aspect of the invention is packaging with an integrated component for controlled dispensing of a flexible elongate tubular product retained within the packaging. The packaging is pliant and defines a product retention chamber.

In a first embodiment of the second aspect of the invention, the dispensing control device includes a main body and a locking member. A passageway extends through the main body and an oblong orifice extends through the locking member. The main body is fixedly attached to the packaging with a first portion positioned within the product retention chamber and a second portion positioned exterior to the product retention chamber so as to provide a port through the packaging. The locking member is hingedly attached to the first portion of the main body for pivoting about a pivot axis and is fixedly secured to the main body so that the major axis of the oblong orifice is fixedly oriented nearly parallel with the pivot axis. The locking member is pivotable about the pivot axis relative to the main body as between a first position wherein the central axis of the orifice is aligned with the central axis of the passageway, and a second position wherein the central axis of the orifice is misaligned with the central axis of the passageway.

In a second embodiment of the second aspect of the invention the flexible elongate tubular product retained within the packaging is an intermittent urinary catheter, and the dispensing control device is disposed at one end of the packaging and includes a main body and a locking member. The main body is attached to the packaging and has longitudinally spaced opposed first and second ends with the first end disposed inside the product retention chamber and the second end disposed outside the product retention chamber. A passageway extends through the main body from the first end to the second end so as to define a port through which the catheter retained within the product retention chamber of the packaging may be dispensed from the packaging. First and second laterally spaced engagement members extend longitudinally from the first end of the main body, with the engagement members positioned on diametric sides of the opening into the passageway. The locking member is hingedly attached at a first lateral end to the first engagement member for pivoting about a pivot axis, and has an oblong orifice there through with a major axis fixedly oriented nearly parallel with the pivot axis. The catheter extends through and is frictionally engaged within the oblong orifice for effecting pivoting of the locking member about the pivot axis upon translational movement of the catheter along the central axis of the catheter as between a first position wherein the locking member contacts the second engagement member with the central axis of orifice aligned with the interior end of the central axis of the port for accommodating passage of the catheter through the orifice, and a second position wherein the central axis of the orifice is misaligned with the interior end of the central axis of the port so as to inhibit passage of the catheter through the orifice. Such pivoting of the locking member functions to control movement of the catheter by permitting withdrawal of the catheter from the packaging through the passageway in the housing, while inhibiting return of a withdrawn length of the catheter into the packaging.

DETAILED DESCRIPTION OF A PREFERRED EMBODIMENT

Figure 1:
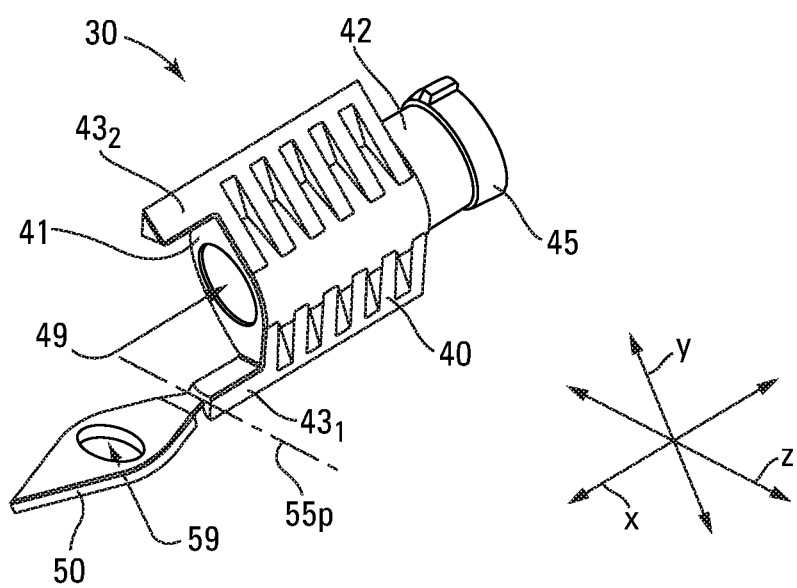
FIG. 1 is a perspective view of one embodiment of the catheter movement control device with the locking member pivoted into the second locking position.
Figure 2:
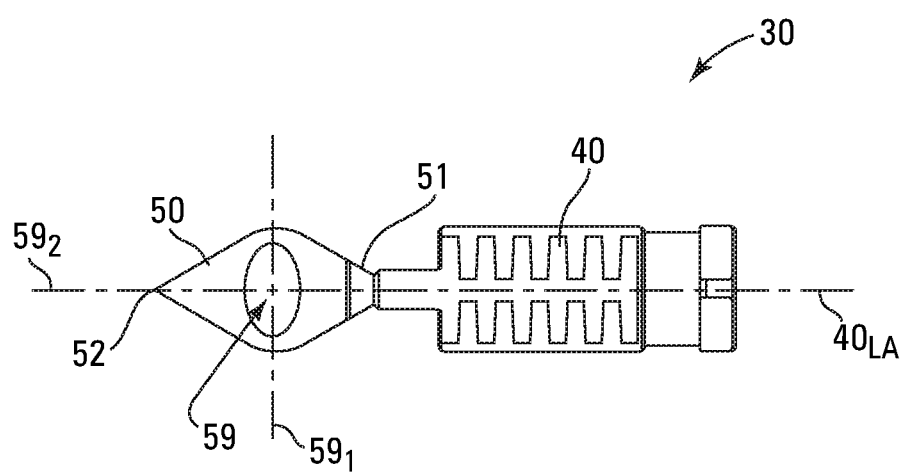
FIG. 2 is a side view of the catheter movement control device depicted in FIG. 1.
Figure 3:
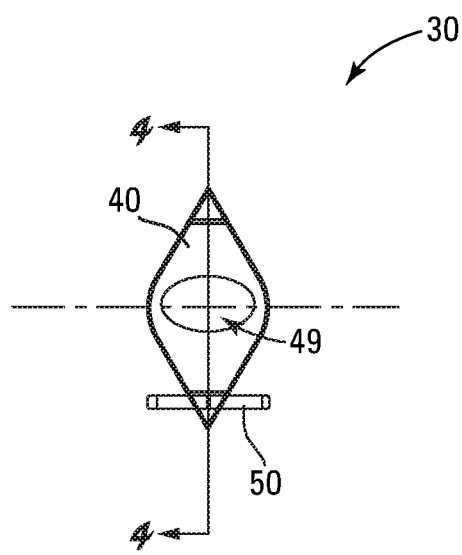
FIG. 3 is an end view of the catheter movement control device depicted in FIG. 1.
Figure 4:
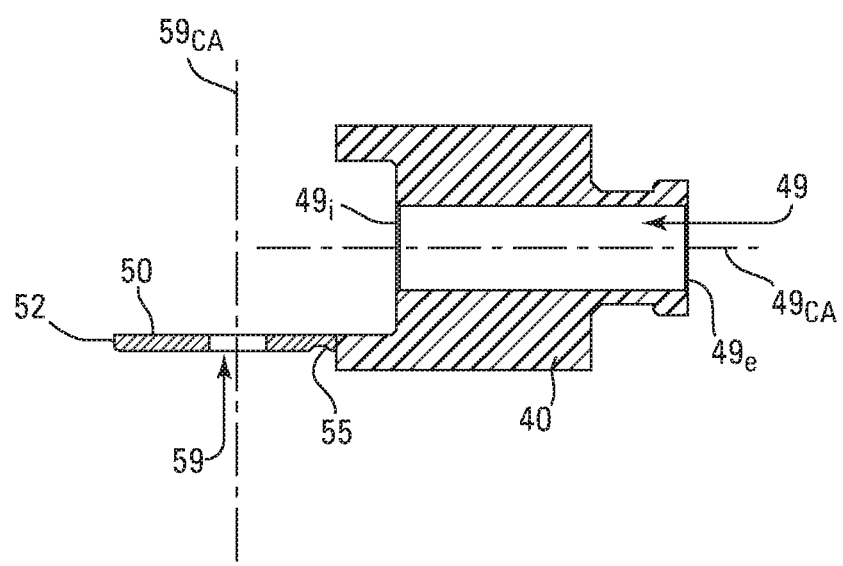
FIG. 4 is a cross-sectional side view of the catheter movement control device depicted in FIG. 1 taken along line 4-4.

Nomenclature
10 Packaged Catheter
20 Packaging
21 First Longitudinal End of Packaging
22 Second Longitudinal End of Packaging
29 Product Retention Chamber
30 Movement Control Device (Dispensing Control Device)
40 Main Body of Movement Control Device
$40_1$ First Portion of Main Body of Movement Control Device
$40_2$ Second Portion of Main Body of Movement Control Device
$40_{LA}$ Longitudinal Axis of Main Body
41 First Longitudinal End of Main Body
42 Second Longitudinal End of Main Body
43 Engagement Members
$43_1$ First Longitudinally Extending Engagement Member
$43_2$ Second Longitudinally Extending Engagement Member
45 Cap or Seal
49 Passageway Through Main Body
49$i$ Interior End (Opening) of Passageway Through Main Body
49$e$ Exterior End (Opening) of Passageway Through Main Body
$49_{CA}$ Central Axis of Passageway
50 Locking Member
51 First or One Lateral End of Locking Member
52 Second or Other Lateral End of Locking Member
55 Hinge
$55_P$ Hinge Pivot Axis
59 Oblong Orifice Though Locking Member
$59_{CA}$ Central Axis of Oblong Orifice
$59_1$ Major Axis of Oblong Orifice
$59_2$ Minor Axis of Oblong Orifice
60 Catheter
61 Lumen End
62 Funnel End
$69_{CA}$ Central Axis of Catheter
$X_1$ First Longitudinal Direction
$X_2$ Second Longitudinal Direction
Y Lateral Direction
Z Transverse Direction Definitions As utilized herein, including the claims, the phrase "nearly parallel" means within 40° of parallel.

As utilized herein, including the claims, the phrase "almost parallel" means within 25° of parallel.

As utilized herein, including the claims, the phrase "essentially parallel" means within 10° of parallel.

As utilized herein, including the claims, the term "aspect ratio" means the ratio of the major or longer dimension to the minor or shorter dimension. For example, when the geometric shape is a rectangle the aspect ratio is the ratio of its longer side to its shorter side. When the geometric shape is an oval the aspect ratio is the ratio of its major axis to its minor axis.

Description
Construction

Referring to FIGS. 1-5, a first aspect of the invention is a catheter movement control device 30. Referring to FIG. 6, a second aspect of the invention is a packaged catheter 10 equipped with a catheter movement control device 30 in accordance with the first aspect of the invention.

The catheter movement control device 30 has a main body 40 and a locking member 50 hingedly attached to the main body 40. The main body 40 and locking member 50 are preferably formed as a monolithic device with the locking member 50 pivoting about a live hinge 55 formed in the single piece device. The locking member 40 may be made from any suitable material, including various plastics such as polyethylene, polypropylene, polyvinyl chloride (PVC), and nylon.

The main body 40 of the catheter movement control device 30 has a first longitudinal end 41 and a second longitudinal end 42, and defines a longitudinal axis $40_{LA}$. A passageway 49 extends through the main body 40 from an opening 49$i$ in the first longitudinal end 41 of the main body 40 to an opening 49$e$ in the second longitudinal end 42 of the main body 40. The passageway 49 is preferably linear and defines a central axis $49_{CA}$. The passageway 49 is sized and configured to allow passage of the lumen end 61 of a catheter 60.

Figure 5:
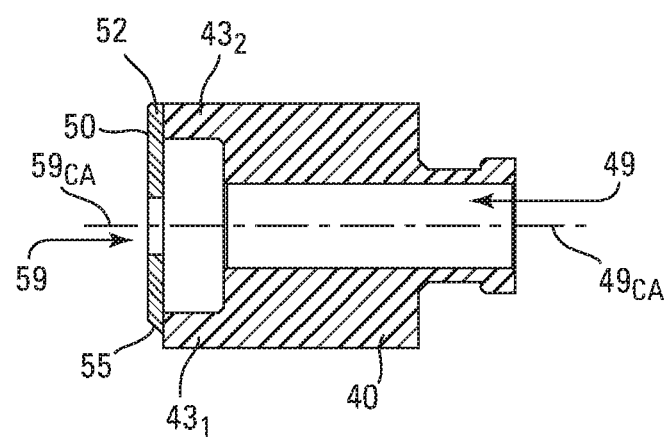
FIG. 5 is a cross-sectional side view of the catheter movement control device depicted in FIG. 1 taken along line 4-4, but with the locking mechanism pivoted into the first dispensing position.
Figure 6:
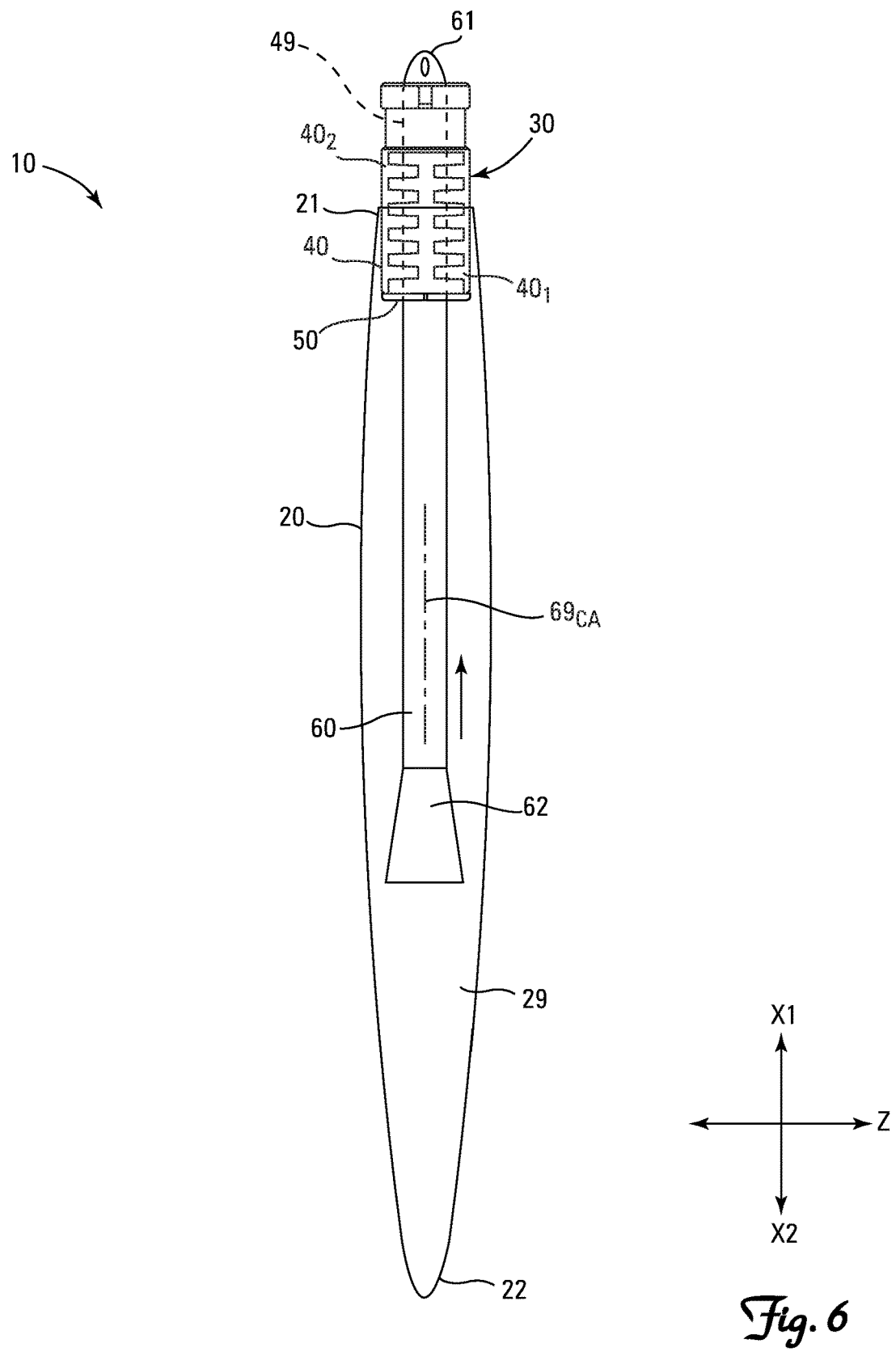
FIG. 6 is a side plan view of a packaged intermittent urinary catheter with an integrated catheter movement control device in accordance with FIGS. 1-5.

A first lateral end 51 of the locking member 50 is hingedly attached to the main body 40 at hinge 55, permitting pivoting of the locking member 50 relative to the main body 40 as between a first aligned position depicted in FIGS. 5 and 6, and a second misaligned position depicted in FIGS. 1-4. In the first aligned position the second lateral end 52 of the locking member 50 contacts the main body 40 and the central axis $59_{CA}$ of the orifice 59 is aligned with the central axis $49_{CA}$ of the passageway 49. When in the first aligned position a catheter 60 may be axially translated through the aligned orifice 59 and passageway 49. Pivoting of the locking member 50 from the first aligned position towards the second misaligned position pivots the second lateral end 52 of the locking member 50 away from the main body 40, resulting in an increasing misalignment of the central axis $59_{CA}$ of the orifice 59 and the central axis $49_{CA}$ of the passageway 49 until movement of a catheter 60 is inhibited through the misaligned orifice 59 and passageway 49.

In a preferred embodiment, laterally y spaced engagement members 43 extend longitudinally x from a longitudinal end of the main body 40, with a first lateral end 51 of the locking member 50 hingedly attached to a first $43_1$ of these engagement members 43 at hinge 55, and the second $43_2$ of these engagement members 43 located to contact the second lateral end 52 of the locking member 50 when the locking member 50 is in the first aligned position. The engagement members 43 provide a modest offset between the passageway 49 and the orifice 59 for avoiding severe bending and kinking of the catheter 60 when the central axis $59_{CA}$ of the orifice 59 and the central axis $49_{CA}$ of the passageway 49 are misaligned.

Pivoting of the locking member 50 about the hinge pivot axis 55$p$ is effected by axial movement of a frictionally engaged catheter 60 through the orifice 59. Referring to FIG. 6, axial translation of a frictionally engaged catheter 60 in the first longitudinal direction $X_1$ out of the packaging 20 causes pivoting of the locking member 50 towards the first aligned position so as to allow axial movement of the catheter 60 out of the package 20 through the aligned central axis $59_{CA}$ of the orifice 59 and the central axis $49_{CA}$ of the passageway 49. In contrast, axial translation of a frictionally engaged catheter 60 in the second longitudinal direction $X_2$ back into the packaging 20 causes pivoting of the locking member 50 towards the second misaligned position so as to resist and impede continued axial movement of the catheter 60 back into the package 20.

Hinge 55 is a fixed position hinge, such as a live hinge, for preventing rotation of the locking member 50 about the central axis $59_{CA}$ of the oblong orifice 59 relative to the main body 40. This locks the oblong orifice 59 into the desired rotational orientation, with its major axis $59_1$ nearly parallel to the hinge pivot axis $55p$, preferably almost parallel to the hinge pivot axis $55p$, and most preferably essentially parallel to the hinge pivot axis $55p$. An absence of such rotational fixation of the locking member 50 to the main body 40 frequently results in a loss of resistance to movement of the catheter 60 in the second direction $X_2$ back into the packaging 20 as dispensing of the catheter 60 has been found to cause the locking member 50 to promptly rotate into an orientation of least resistance, with the major axis $59_1$ of the oblong orifice 59 perpendicular to the hinge pivot axis $55p$, which diminishes the ability of the misaligned locking member 50 to resist axial movement of the catheter 60 in the second direction $X_2$ through the oblong orifice 59 and back into the packaging 20.

As noted, the catheter 60 must be frictionally engaged within the orifice 59 to effect pivoting of the locking member 50. Use of an oblong orifice 59 allows a range of catheters 60 to pass through while frictionally engaging the orifice 59, requiring only that the diameter of the catheter 60 be at least as large as the minor axis $59_2$ of the oblong orifice 59, and the cross-sectional area of the catheter 60 be equal to or less than the cross-sectional area of the oblong orifice 59. A catheter 60 having a diameter smaller than the minor axis $59_2$ of the oblong orifice 59 will not reliably frictionally engage and pivot the locking member 50 upon axial translation of the catheter 60, while a catheter 60 with a cross-sectional area greater than the cross-sectional area of the oblong orifice 59 simply won't fit through the oblong orifice 59 despite its ability to elastically deform to fit the shape of the oblong orifice 59.

The oblong orifice 59 through the locking member 50 defines a central axis $59_{CA}$. The elastic nature of catheters (i.e., the ability to readily and temporarily deform from a generally circular cross-section to an oblong cross-section) allows catheters 60 of different diameters to readily frictionally pass through the oblong orifice 59. The oblong orifice 59 can have substantially any oblong shape, with rectangular and oval shapes generally preferred. The oblong orifice 59 preferably has a major axis $59_1$ to minor axis $59_2$ aspect ratio of between 1.2:1 to 3:1, most preferably between 1.5:1 to 2:1. A ratio smaller than 1.2:1 unnecessarily limits the range of catheter sizes that can be successfully used with the same movement control device 30, while a ratio larger than 3:1 does not produce an appreciable increase the range of catheter sizes that can be successfully used with the movement control device 30 as the frictional engagement alone resulting from the extensive deformation required to fit a larger catheter 60 into such a high aspect ratio orifice 59 unreasonably hinders dispensing of the catheter 60 even when the locking member 50 is pivoted into the first aligned position.

The size and dimensions of the movement control device 30 are generally dictated by the size of the catheter 60 with which it is used, but the main body 40 should be large enough to be retentively pinched between the thumb and index finger in order to allow dispensing of the catheter 60 from the packaging 20 through the movement control device 30. Dimensions of an exemplary movement control device 30 are provided in Table One below.

TABLE ONE (Exemplary Dimensions)

| DIMENSION | SIZE |
| --- | --- |
| Longitudinal Length of Main Body 40 | 25 mm |
| Lateral Width of Main Body 40 | 20 mm |
| Transverse Depth of Main Body 40 | 10 mm |
| Cross Sectional Area of Passageway 49 | 200 mm$^2$ |
| Thickness of Locking Member 50 | 1-2 mm |
| Cross Sectional Area of Orifice 59 | 100 mm$^2$ |

Referring to FIG. 6, when incorporated into a packaged catheter 10, the catheter movement control device 30 is fixedly attached to the packaging 20 with a first portion $40_1$ of the main body 40 positioned within the product retention chamber 29 defined by the packing 20, and a second portion $40_2$ of the main body 40 positioned exterior to the product retention chamber 29. The passageway 49 through the main body 40 provides a port through the packaging 20 from an interior end $49i$ of the passageway 49 to an exterior end $49e$ of the passageway 49. The movement control device 30 can conveniently be heat sealed at a longitudinal end 21 of the packaging 20. A cap or seal 45 can be placed over the exterior end $49e$ of the passageway 49.

The catheter 60 may have any desired longitudinal length and shape effective for achieving the function of eliminating urine from the bladder of a male or female patient. Preferably, the longitudinal length for an adult female catheter 60 is between 2-6 inches, the longitudinal length of the adult male catheter 60 is between 10-16 inches, and the longitudinal length of a pediatric catheter 60 is between 5-11 inches.

Use

The packaged intermittent urinary catheter 10 can be used by patients for self catheterization. Prior to use the patient should take all sanitary procedures advised by their doctors to decrease the risks of infection.

First, the seal or cap 45 is removed to open the port through the packaging 20 defined by the passageway 49 through the main body 40 of the movement control device 30.

The user then grasps or pinches the main body 40 of the movement control device 30 with one hand, grasps or pinches the catheter 60 through the packaging 20 at a location below the locking member 50, and then pushes the catheter 60, along with the packaging 20, in the first longitudinal direction $X_1$ towards the passageway 49 in the main body 40 of the movement control device 30. This translational movement of the catheter 60 causes the locking member 50 to pivot into the aligned first position until the second lateral end 52 of the locking member 50 contacts the main body 40 so as to align the central axis $59_{CA}$ of the orifice 59 with the central axis $49_{CA}$ of the passageway 49. This aligned orientation allows continued movement of the catheter 60 in the first longitudinal direction $X_1$ out of the packaging 20 for insertion into the urethra of a user.

When a user releases the catheter 60 in order to move his/her grip further down the catheter 60 to continue dispensing of the catheter 60, or the catheter 60 encounters resistance during insertion, the catheter 60 will tend to experience a reaction force tending to push the catheter 60 in the second longitudinal direction $X_2$ back into the packaging 20. Such retraction of the catheter 60 during insertion is undesirable. The movement control device 30 limits such movement in the second longitudinal direction $X_2$ back in the packaging 20 as such backward movement of the catheter 60 causes the locking member 50 to pivot towards the second misaligned position and resist continued movement of the catheter 60 in the second longitudinal direction $X_2$.

The movement control device 30 also functions to preventing the funnel end 72 of the catheter 70 from advancing out of the package 20.

I claim:

1. A catheter movement control device, comprising:
   (a) a main body having a passageway extending through the main body and defining a central axis, and
   (b) a locking member hingedly attached to the main body for pivoting about a pivot axis, the locking member having an oblong orifice there through defining respective central, major and minor axes, each axis orthogonal to the other two axes, with the major axis fixedly oriented nearly parallel with the pivot axis,
   (c) wherein the locking member is pivotable about the pivot axis relative to the main body as between a first position wherein the central axis of the orifice is aligned with the central axis of the passageway, and a second position wherein the central axis of the orifice is misaligned with the central axis of the passageway.

2. The catheter movement control device of claim 1 wherein the major axis is fixedly oriented almost parallel with the pivot axis.

3. The catheter movement control device of claim 1 wherein the major axis is fixedly oriented essentially parallel with the pivot axis.

4. The catheter movement control device of claim 1 wherein the oblong orifice through the locking member has an aspect ratio of between 1.2:1 to 3:1.

5. The catheter movement control device of claim 1 wherein the oblong orifice through the locking member has an aspect ratio of between 1.5:1 to 2:1.

6. The catheter movement control device of claim 1 wherein the locking member is planar.

7. Packaging with an integrated component for controlled dispensing of a flexible elongate tubular product retained within the packaging, comprising:
   (a) pliant packaging defining a product retention chamber, and
   (b) a dispensing control device, the dispensing control device including at least:
      (i) a main body fixedly attached to the packaging with (i) a first portion positioned within the retention chamber, (ii) a second portion positioned exterior to the retention chamber, and (iii) a passageway extending through the main body so as to provide a port having an interior end and an exterior end through the packaging, and
      (ii) a locking member hingedly attached to the main body for pivoting about a pivot axis, the locking member having an oblong orifice there through defining respective central, major and minor axes, each axis orthogonal to the other two axes, with the major axis fixedly oriented nearly parallel with the pivot axis,
      (iii) wherein the port defines a central axis, with the locking member pivotable about the pivot axis relative to the main body as between a first position wherein the central axis of the orifice is aligned with the interior end of the central axis of the port, and a second position wherein the central axis of the orifice is misaligned with the interior end of the central axis of the port.

8. The packaging of claim 7 wherein the major axis is fixedly oriented almost parallel with the pivot axis.

9. The packaging of claim 7 wherein the major axis is fixedly oriented essentially parallel with the pivot axis.

10. The packaging of claim 7 wherein the oblong orifice through the locking member has an aspect ratio of between 1.2:1 to 3:1.

11. The packaging of claim 7 wherein the oblong orifice through the locking member has an aspect ratio of between 1.5:1 to 2:1.

12. The packaging of claim 7 further comprising an intermittent urinary catheter retained within the package.

13. The packaging of claim 7 wherein the locking member is planar.

14. A packaged intermittent urinary catheter, comprising:
   (a) pliant packaging defining a product retention chamber,
   (b) an intermittent urinary catheter within the product retention chamber, the catheter defining a central axis, and
   (c) a catheter movement control device disposed at one end of the packaging, the catheter movement control device including at least:
      (i) a main body attached to one end of the packaging, the main body having:
         (1) longitudinally spaced opposed first and second ends with the first end disposed inside the product retention chamber and the second end disposed outside the product retention chamber,
         (2) a passageway through the main body extending between an opening in the first end of the main body and an opening in the second end of the main body, the passageway defining a port through which the catheter retained within the product retention chamber of the packaging may be dispensed from the packaging, and
         (3) first and second laterally spaced engagement members extending longitudinally from the first end of the main body, the engagement members positioned on diametric sides of the opening in the first end of the main body, and
      (ii) a locking member hingedly attached at a first lateral end to the first engagement member for pivoting about a pivot axis, the locking member having an oblong orifice there through, defining respective central, major and minor axes, each axis orthogonal to the other two axes, with the major axis fixedly oriented nearly parallel with the pivot axis,
      (iii) wherein the catheter extends through and is frictionally engaged within the oblong orifice for effecting pivoting of the locking member about the pivot axis upon translational movement of the catheter along the central axis of the catheter as between a first position wherein the locking member contacts the second engagement member with the central axis of the orifice aligned with the interior end of the central axis of the port for accommodating passage of the catheter through the orifice, and a second position wherein the central axis of the orifice is misaligned with the interior end of the central axis of the port so as to inhibit passage of the catheter through the orifice,
      (iv) whereby the catheter movement control device permits withdrawal of the catheter from the packaging through the passageway in the housing, while inhibiting return of a withdrawn length of the catheter into the packaging.

15. The packaged intermittent urinary catheter of claim 14 wherein the major axis is fixedly oriented almost parallel with the pivot axis.

16. The packaged intermittent urinary catheter of claim 14 wherein the major axis is fixedly oriented essentially parallel with the pivot axis.

17. The packaged intermittent urinary catheter of claim 14 wherein the oblong orifice through the locking member has an aspect ratio of between 1.2:1 to 3:1.

18. The packaged intermittent urinary catheter of claim 14 wherein the oblong orifice through the locking member has an aspect ratio of between 1.5:1 to 2:1.

19. The packaged intermittent urinary catheter of claim 14 wherein the locking member is planar.

\* \* \* \* \*